United States Patent
Yang

(10) Patent No.: US 11,945,958 B2
(45) Date of Patent: Apr. 2, 2024

(54) METHOD FOR FABRICATING COLLAGEN BIO-INK, COLLAGEN BIO-INK AND 3D BIO-PRINTING METHOD

(71) Applicant: HORIEN BIOCHEMICAL TECHNOLOGY CO., LTD., Taichung (TW)

(72) Inventor: Hsi-Min Yang, Taichung (TW)

(73) Assignee: Horien Biochemical Technology Co., Ltd., Taichung (TW)

( * ) Notice: Subject to any disclaimer, the term of this patent is extended or adjusted under 35 U.S.C. 154(b) by 0 days.

(21) Appl. No.: 17/855,852

(22) Filed: Jul. 1, 2022

(65) Prior Publication Data
US 2023/0040223 A1 Feb. 9, 2023

(30) Foreign Application Priority Data

Jul. 30, 2021 (TW) ................. 110128229
Apr. 14, 2022 (TW) ................. 111114345

(51) Int. Cl.
C09D 11/04 (2006.01)
B33Y 10/00 (2015.01)
B33Y 70/00 (2020.01)
B33Y 80/00 (2015.01)

(52) U.S. Cl.
CPC .............. *C09D 11/04* (2013.01); *B33Y 10/00* (2014.12); *B33Y 70/00* (2014.12); *B33Y 80/00* (2014.12)

(58) Field of Classification Search
None
See application file for complete search history.

(56) References Cited

U.S. PATENT DOCUMENTS

| | | | |
|---|---|---|---|
| 2016/0193384 A1* | 7/2016 | Phopase | C08J 3/075 514/772.4 |
| 2019/0106673 A1* | 4/2019 | Skardal | A61L 27/54 |
| 2020/0297897 A1* | 9/2020 | Sundararaj | A61L 27/425 |
| 2021/0299330 A1* | 9/2021 | Utama | A61L 27/26 |

\* cited by examiner

*Primary Examiner* — Mohammad M Ameen
(74) *Attorney, Agent, or Firm* — Joseph C. Zucchero; Carolyn S. Elmore; Elmore Patent Law Group

(57) ABSTRACT

A method for fabricating a collagen bio-ink includes steps as follows. A first component is provided, wherein the first component is to fill a collagen powder to a first syringe. A second component is provided, wherein the second component is to fill a neutral solution or an acid solution to a second syringe. A mixing step is performed, wherein the first syringe is connected to the second syringe with a Lure lock connector and pushing back and forth to mix the first component and the second component to form a hydrogel and become a collagen bio-ink.

7 Claims, 14 Drawing Sheets
(3 of 14 Drawing Sheet(s) Filed in Color)

100 a first component is provided — 110 a second component is provided — 120 a mixing step is performed — 130

METHOD FOR FABRICATING COLLAGEN BIO-INK, COLLAGEN BIO-INK AND 3D BIO-PRINTING METHOD

RELATED APPLICATIONS

This application claims priority to Taiwan Application Serial Number 110128229, filed Jul. 30, 2021 and Taiwan Application Serial Number 111114345, filed Apr. 14, 2022, which is herein incorporated by reference.

BACKGROUND

Technical Field

The present disclosure relates to a method for fabricating a bio-ink. More particularly, the present disclosure relates to a method for fabricating a collagen bio-ink, a collagen bio-ink and a 3D bio-printing method.

Description of Related Art

Three-dimensional bio-printing is used to fabricate the various artificial structures with predetermined structures or performing specific functions by bio-ink and layered manufacturing method. Therefore, three-dimensional bio-printing can repair or reconstruct human tissues or organs, which has great application in the fields of medical treatment and tissue engineering.

Furthermore, the main core element of 3D bio-printing is the preparation of bio-ink. The conventional bio-ink is formed by the combination of hydrogel, cells and growth factors, and is shaped by the nozzle. However, because the bio-ink needs to load the cells and support the overall structure, the ideal bio-ink needs to have the ability of rapid forming, mild reaction conditions and biocompatibility, and the product can be printed with high structural stability, bio-applicability and specific functions of organization.

Therefore, the industry is still looking for a bio-ink, which has the characteristics, such as biocompatibility, specific rheological property and preservability to print the artificial structure with structural stability and biocompatibility.

SUMMARY

According to one aspect of the present disclosure, a method for fabricating a collagen bio-ink includes steps as follows. A first component is provided, wherein the first component is to fill a collagen powder to a first syringe. A second component is provided, wherein the second component is to fill a neutral solution or an acid solution to a second syringe. A mixing step is performed, wherein the first syringe is connected to the second syringe with a Lure lock connector and pushing back and forth to mix the first component and the second component to form a hydrogel and become a collagen bio-ink.

According to another aspect of the present disclosure, a collagen bio-ink is to provided. The collagen bio-ink is fabricated by the method according to the aforementioned aspect.

According to further aspect of the present disclosure, a 3D bio-printing method includes steps as follows. The collagen bio-ink according to the aforementioned aspect is provided. A 3D printing step is performed, wherein the collagen bio-ink is injected into a bio-printer, and the collagen bio-ink is squeezed for printing by using an extrusion needle to obtain a 3D bio-printing structure.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

The present disclosure will be further exemplified by the following specific embodiments. However, the embodiments can be applied to various inventive concepts and can be embodied in various specific ranges. The specific embodiments are only for the purposes of description, and are not limited to these practical details thereof.

Figure 1:
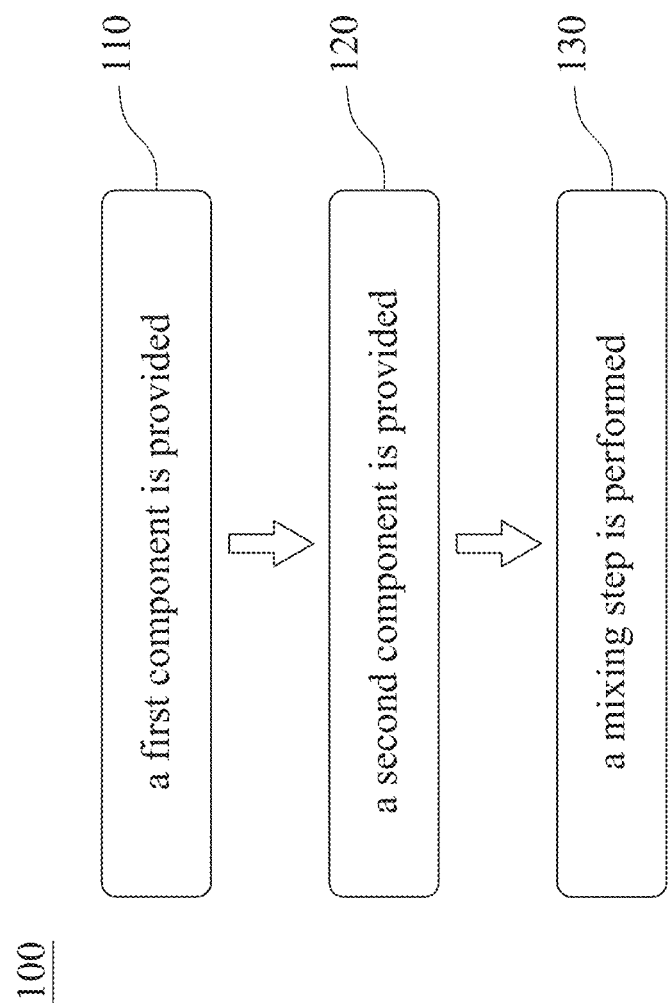
FIG. 1 is a flow chart of a method for fabricating a collagen bio-ink according to one embodiment of the present disclosure.
Figure 2:
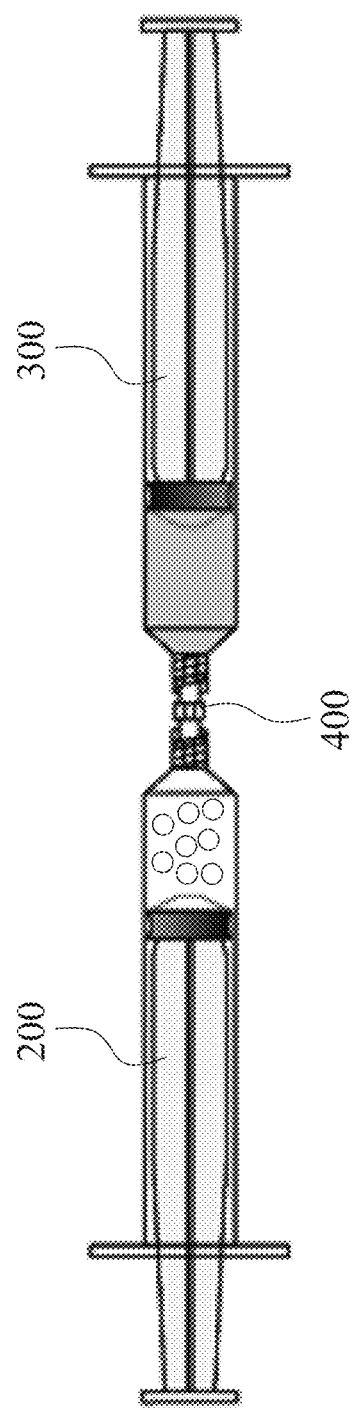
FIG. 2 is a process diagram of the method for fabricating the collagen bio-ink of FIG. 1.

Please refer to FIG. 1 and FIG. 2, wherein FIG. 1 is a flow chart of a method for fabricating a collagen bio-ink 100 according to one embodiment of the present disclosure. FIG. 2 is a process diagram of the method for fabricating the collagen bio-ink 100 of FIG. 1. In FIG. 1, the method for fabricating the collagen bio-ink 100 includes a step 110, a step 120 and a step 130.

In the step 110, a first component is provided, wherein the first component is to fill a collagen powder to a first syringe 200. Specifically, the collagen accounts for more than 30% of the human protein, and simultaneously the collagen is also the primary component of the extracellular matrix and has the excellent biocompatibility which allows the plausibility of applying collagen in the tissue engineering or 3D printing technology. Therefore, the present disclosure uses collagen for the primary component of the bio-ink.

In the present disclosure, the extraction source for the collagen can be bovine, porcine, marine or cells, etc., and using the freeze-drying granulation technology to prepare the collagen powder. The moisture content of the collagen powder is less than 10%, pH value is 3.0 to 8.0, and the collagen powder can be preserved and transported in the vacuum packaging, wherein the temperature of effective preserve and transport can be 25° C. Furthermore, the first component can further include a gelatin powder to Increase the reconstitute level and swelling capacity of the collagen bio-ink during preparation, the printability and the degree of support structure after printing. Preferably, when preparing the collagen bio-ink with a concentration less than 6% w/v, the gelatin powder can be added, wherein a ratio of the collagen powder to the gelation powder can be 10:1.

The collagen bio-ink sold on the current market is prefilled into a container for transportation and preservation by a colloidal based system mainly. Due to the high moisture content of the colloidal based system, the collagen bio-ink is easy to deteriorate by the factors, such as temperature rise and preserve condition. However, the present disclosure uses the collagen powder for filling. Due to the low moisture content of the collagen powder, the transportation and preserve condition are better than that of the collagen bio-ink of the colloidal based system. At the same time, using the powder system can achieve the free compounding of the collagen concentration of the bio-ink and the type of the solution.

In the step 120, a second component is provided, wherein the second component is to fill a neutral solution or an acid solution to a second syringe 300. The neutral solution can be but not limited to cell culture medium, normal saline or ultrapure water, such as phosphate buffered saline (PBS) or Dulbecco's modified minimal essential medium (DMEM).

In the step 130, a mixing step is performed, wherein the first syringe 200 is connected to the second syringe 300 with a Lure lock connector 400 and pushing back and forth to mix the first component and the second component to form a hydrogel and become a collagen bio-ink.

Specifically, if the second component is the acid solution, a neutralization step can be performed, wherein after the acid solution mixed with the collagen powder, a buffer salt solution, an alkaline substance or a conjugated acidic base pair is added to neutralize acidic level, so that the collagen bio-ink is kept in a neutral state.

Furthermore, after the mixing step, an adding step can be performed, wherein a functional solution or a cell solution is added to the collagen bio-ink. The functional solution can be but not limited to a medicine, a growth factor or a cross-linking agent solution. The present disclosure uses the genipin as the cross-linking agent solution. The genipin is a natural cross-linking agent solution, which can be cross-linked with the collagen, and has the characteristics of great biocompatibility. Moreover, the addition of the cell solution can be used to observe whether the collagen bio-ink has bio-applicability.

Figure 3:
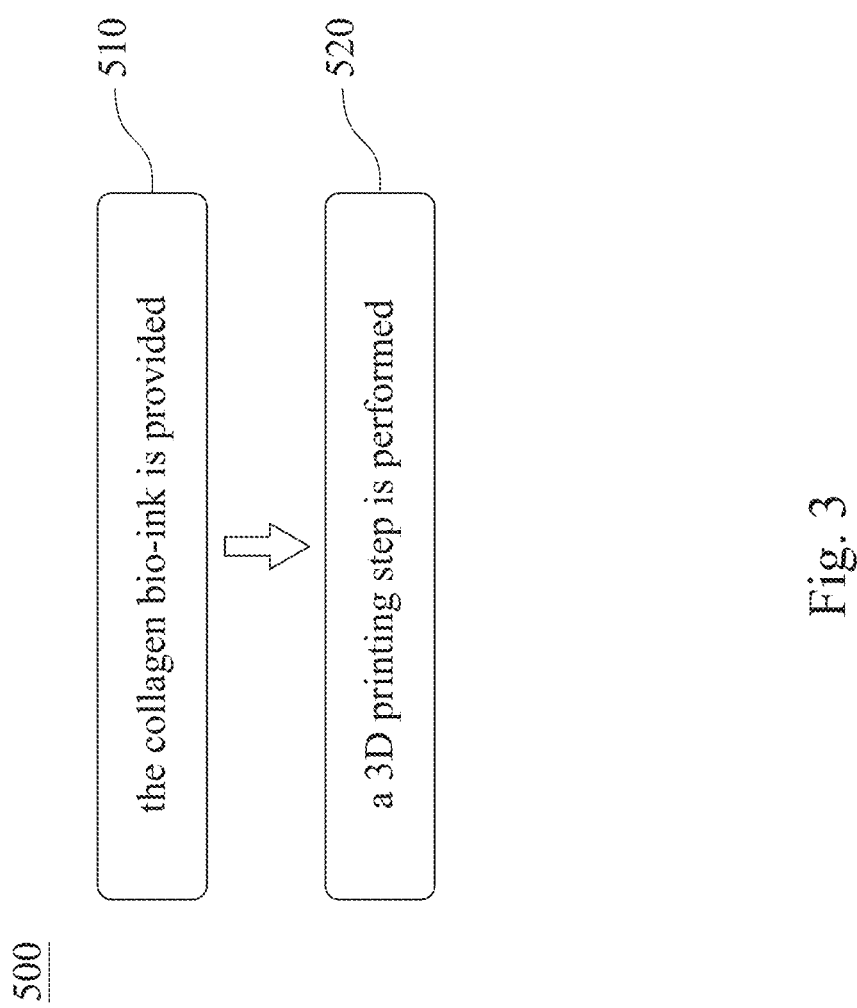
FIG. 3 is a flow chart of a 3D bio-printing method according to another embodiment of the present disclosure.

Therefore, the present disclosure further provides a collagen bio-ink fabricated by the aforementioned method, which can be used to perform a 3D bio-printing. Please refer to FIG. 3, which is a flow chart of a 3D bio-printing method 500 according to another embodiment of the present disclosure. In FIG. 3, the 3D bio-printing method 500 includes a step 510 and a step 520.

In the step 510, the collagen bio-ink is provided. Then, in the step 520, a 3D printing step is performed, wherein the collagen bio-ink is injected into a bio-printer, and the collagen bio-ink is squeezed for printing by using an extrusion needle to obtain a 3D bio-printing structure.

Specifically, the present disclosure uses the extrusion-based bio-printing to perform the 3D bio-printing technology, the method mainly uses an air pump or a mechanical screw to generate pressure to extrude the collagen bio-ink by the extrusion needle and stack into the predetermined structure on the printing platform. The advantage of the extrusion-based bio-printing is that the needles can be selected with different inner diameters, and the pressure intensity and the temperature can be adjusted to control the printing speed and the resolution. In the present disclosure, the extrusion needle of the bio-printer can be but not limited to a dispensing nozzle or a stainless steel blunt needle, and a temperature of the 3D printing step can range from 4° C. to 25° C.

Furthermore, before the 3D printing step, a preserving step can be performed, wherein the prepared collagen bio-ink is preserved below a temperature of 4° C., so that the collagen bio-ink swells into a solid gel state at the low temperature, and then takes out when the 3D printing step is performed.

The present disclosure will be further exemplified by the following specific embodiments so as to facilitate utilizing and practicing the present disclosure completely by the people having ordinary skill in the art without over-interpreting and over-experimenting. However, the readers should understand that the present disclosure should not be limited to these practical details thereof, that is, these practical details are used to describe how to implement the materials and methods of the present disclosure and are not necessary.

EXAMPLE

The method for fabricating the collagen bio-ink of Example 1 to Example 3 of the present disclosure is to fill the collagen powder to the first syringe, then fill 1×PBS solution to the second syringe. Next, the first syringe is connected to the second syringe with the Lure lock connector and pushing back and forth 40 to 50 times until the collagen powder mixed with 1×PBS solution to form the hydrogel. The contents of the first component and the second component of Example 1 to Example 3 are shown in Table 1.

TABLE 1

|  | Example 1 | Example 2 | Example 3 |
|---|---|---|---|
| first component | 0.3 g | 0.6 g | 0.9 g |
| second component | 10 mL | 10 mL | 10 mL |
| concentration | 3% w/v | 6% w/v | 9% w/v |

The method for fabricating the collagen bio-ink of Example 4 of the present disclosure is to fill 0.6 g of the collagen powder and 0.06 g of the gelatin powder (sourced from pig skin) to the first syringe, then fill 10 mL of 1×PBS solution to the second syringe.

Next, the first syringe is connected to the second syringe with the Lure lock connector and pushing back and forth 40 to 50 times until the collagen powder and the gelatin powder mixed with 1×PBS solution to form the hydrogel.

The method for fabricating the collagen bio-ink of Example 5 to Example 7 of the present disclosure is to fill 0.6 g of the collagen powder and 0.06 g of the gelatin powder (sourced from pig skin) to the first syringe, then fill 8 mL of 1×PBS solution to the second syringe. Next, the first syringe is connected to the second syringe with the Lure lock connector and pushing back and forth 40 to 50 times until the collagen powder and the gelatin powder mixed with 1×PBS solution to form the hydrogel, and stored in the first syringe. After that, the genipin powder is filled to the third syringe and 2 mL of 1×PBS solution is added to mix evenly to form the cross-linking agent solution for backup use. Next, the first syringe is connected to the third syringe with the Lure lock connector and pushing back and forth 40 to 50 times to mix evenly the collagen and the gelatin solution with the cross-linking agent solution. The contents of the genipin powder and the concentrations of the cross-linking agent solution of Example 5 to Example 7 are shown in Table 2.

TABLE 2

|  | Example 5 | Example 6 | Example 7 |
|---|---|---|---|
| genipin powder | 0.01 g | 0.04 g | 0.08 g |
| cross-linking agent solution concentration | 0.1% w/v | 0.4% w/v | 0.8% w/v |

The method for fabricating the collagen bio-ink of Example 8 of the present disclosure is to fill 0.6 g of the collagen powder to the first syringe, then fill 10 mL of DMEM medium solution to the second syringe. Next, the first syringe is connected to the second syringe with the Lure lock connector and pushing back and forth 40 to 50 times until the collagen powder mixed with DMEM medium solution to form the hydrogel.

The method for fabricating the collagen bio-Ink of Example 9 to Example 14 of the present disclosure is to fill 0.6 g of the collagen powder to the first syringe, then fill 10 mL of 1×PBS solution to the second syringe. Next, the first syringe is connected to the second syringe with the Lure lock connector and pushing back and forth 40 to 50 times until the collagen powder mixed with 1×PBS solution to form the hydrogel. Then, the collagen bio-ink of 6% w/v concentration is diluted with 1×PBS solution to the concentration of 1% w/v to 5% w/v for backup use. After that, 0.8 mL of the collagen bio-ink of 1% w/v to 6% w/v concentration is filled to the third syringe, and 0.2 mL of the L929 cell solution is filled to the fourth syringe. Next, the third syringe is connected to the fourth syringe with the Lure lock connector and pushing back and forth 20 times until the collagen bio-ink mixed with the L929 cell solution evenly. The concentrations of the collagen bio-ink of Example 9 to Example 14 are shown in Table 3.

TABLE 3

|  | collagen bio-ink concentration |
|---|---|
| Example 9 | 1% w/v |
| Example 10 | 2% w/v |
| Example 11 | 3% w/v |
| Example 12 | 4% w/v |
| Example 13 | 5% w/v |
| Example 14 | 6% w/v |

The method for fabricating the collagen bio-Ink of Example 15 to Example 21 of the present disclosure is to fill 0.6 g of the collagen powder to the first syringe, then fil 5 mL of the acetic acid solution to the second syringe. Next, the first syringe is connected to the second syringe with the Lure lock connector and pushing back and forth 40 to 50 times until the collagen powder mixed with the acetic acid solution to form the hydrogel, and stored in the first syringe. After that, the PBS solution with pH value of 7.4 is filled to the third syringe, and the first syringe is connected to the third syringe with the Lure lock connector and pushing back and forth 40 to 50 times to mix the collagen and the acetic acid solution with the PBS solution evenly. The concentrations of the acetic acid solution, the contents of PBS solution, the concentrations of the collagen bio-ink and the pH values of Example 15 to Example 21 are shown in Table 4.

TABLE 4

|  | acetic acid solution concentration | PBS solution content | collagen bio-ink concentration | collagen bio-ink pH value |
|---|---|---|---|---|
| Example 15 | 0.025M | 5 mL | 6% w/v | 5.26 |
| Example 16 | 0.025M | 7 mL | 5% w/v | 5.52 |
| Example 17 | 0.025M | 10 mL | 4% w/v | 6.00 |
| Example 18 | 0.025M | 15 mL | 3% w/v | 6.37 |
| Example 19 | 0.0125M | 5 mL | 6% w/v | 6.17 |
| Example 20 | 0.0125M | 7 mL | 5% w/v | 6.47 |
| Example 21 | 0.0125M | 10 mL | 4% w/v | 6.66 |

The method for fabricating the collagen bio-ink of Example 22 of the present disclosure is to fill 0.6 g of the collagen powder to the first syringe, then fill 10 mL of 1×PBS solution to the second syringe to prepare the collagen bio-ink of 6% w/v concentration. Next, the first syringe is connected to the second syringe with the Lure lock connector and pushing back and forth 40 to 50 times until the collagen powder mixed with 1×PBS solution to form the hydrogel, and stored in a refrigerator at 4° C. overnight. Then, 3 mL of the collagen bio-ink of 6% w/v concentration is filed to the third syringe, and 300 μL of the L929 cell solution is filled to the fourth syringe. Next, the third syringe is connected to the fourth syringe with the Lure lock connector and pushing back and forth 30-40 times until the collagen bio-ink mixed with the L929 cell solution evenly.

Rheological Property Measurement

Figure 4:
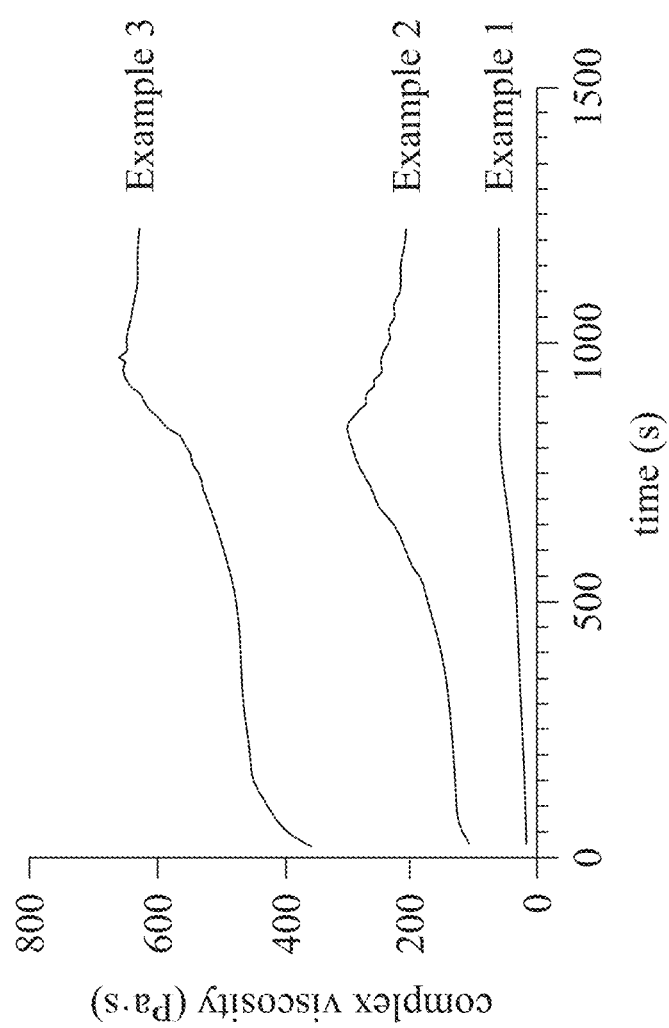
FIG. 4 is a graph of complex viscosity-vs.-time of Example 1 to Example 3.
Figures 5, 6:
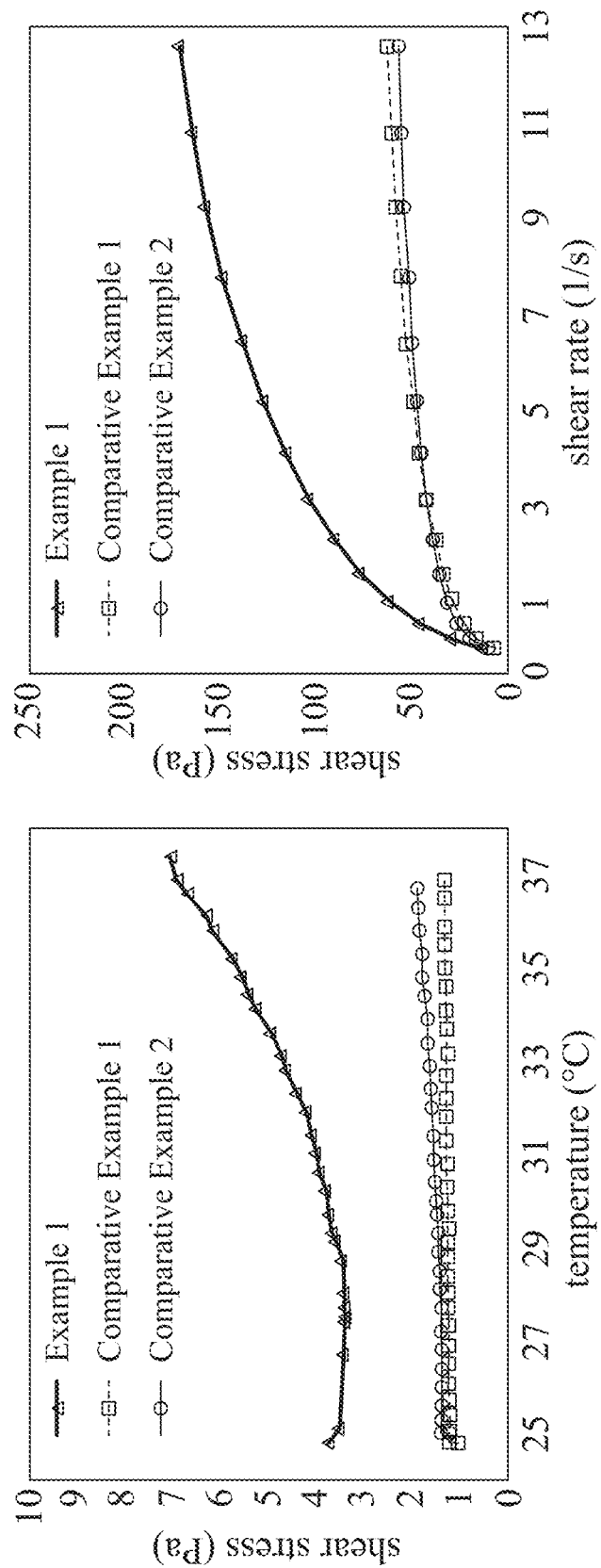
FIG. 5 is a graph of shear stress-vs.-temperature of Example 1 versus Comparative Example 1 and Comparative Example 2.
FIG. 6 is a graph of shear stress-vs.-shear rate of Example 1 versus Comparative Example 1 and Comparative Example 2.

In order to evaluate the rheological property of the collagen bio-ink, a rheometer is used to measure the rheological parameters of the collagen bio-ink. Please refer to FIG. 4, FIG. 5 and FIG. 6, wherein FIG. 4 is a graph of complex viscosity-vs.-time of Example 1 to Example 3. FIG. 5 is a graph of shear stress-vs.-temperature of Example 1 versus Comparative Example 1 and Comparative Example 2. FIG. 6 is a graph of shear stress-vs.-shear rate of Example 1 versus Comparative Example 1 and Comparative Example 2. Comparative Example 1 is the neutral collagen, and Comparative Example 2 is the product Lifeink 200, which is prepared by the colloidal based system.

In FIG. 4, under the condition of the temperature is raised from 10° C. to 37° C., the frequency is 1 Hz and acting 30 minutes (10 minutes for heating and 10 minutes for maintaining at 37° C.), the viscosity performance of the collagen bio-ink of Example 1 to Example 3 to the temperature can be increased from 60 Pa-s to 660 Pa-s, proving that the collagen bio-ink of the present disclosure can be applied in the wide range.

In FIG. 5, under the condition of the temperature is raised from 25° C. to 37° C., the frequency is 1 Hz and acting 4 minutes, the shear stress performance of Example 1 to the temperature can be reached to 7 Pa, which is significantly better than that of Comparative Example 1 and Comparative Example 2, and the hot forming characteristic of Example 1 is better than that of Comparative Example 1 and Comparative Example 2.

In FIG. 6, under the condition of the temperature is 25° C., the strain is 10%, the frequency is ranged from 0.1 Hz to 10 Hz and acting 4 minutes, Example 1, Comparative Example 1 and Comparative Example 2 all show the pseudoplastic fluid characteristic required for 3D printing, that is shear thinning effect. However, at the same shear rate, Example 1 requires greater shear stress and the mechanical strength is better, proving that the collagen bio-ink of the present disclosure has better mechanical strength than that of the commercial product of Comparative Example 2.

Furthermore, the printing rheology of Example 15 to Example 21 is measured, and the results are shown in Table 5. It can be seen from Table 5, the mixing method of the acidic solution mixed with the collagen powder first and then neutralized its acidity, the better colloidal viscosity can be obtained when the concentration of the collagen bio-ink is 5% w/v or more.

TABLE 5

|  | printing rheology |
| --- | --- |
| Example 15 | good |
| Example 16 | fair |
| Example 17 | poor |
| Example 18 | very poor |
| Example 19 | good |
| Example 20 | fair |
| Example 21 | poor |

Printability Measurement

The collagen bio-ink of the present disclosure can be used for 3D bio-printing at the room temperature. For example, the three-dimensional pattern can be completed in advance as the blueprint, and the collagen bio-ink can be squeezed to filamentous hydrogel through the extrusion needle by the bio-printer connected to the computer, so that the predetermined structure is stacked on the printing platform.

Figure 7:
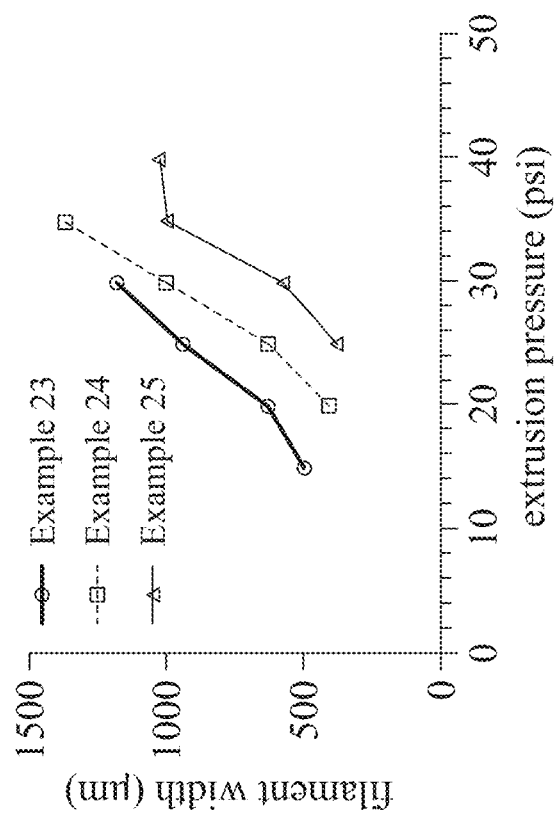
FIG. 7 is a graph of filament width-vs.-extrusion pressure of Example 23 to Example 25.

Please refer to FIG. 7, which is a graph of filament width-vs.-extrusion pressure of Example 23 to Example 25. Specifically, Example 23 to Example 25 are Example 3 by using the dispensing nozzle with inner diameters of 25 G, 27 G and 30 G, respectively, and the single-layer grid (5×5 mm) is printed out at the printing speed of 30 mm/s. Next, after the width of the grid lines shot by the optical microscope, using imageJ software to measure the actual width of the printed lines under different extrusion pressure. It can be seen from the result of FIG. 7, Example 3 has the printability, and the selection of different inner diameters extrusion needle and extrusion pressures will affect the filament width, which can determine the resolution and patter fidelity of the printed product.

Figure 8A:
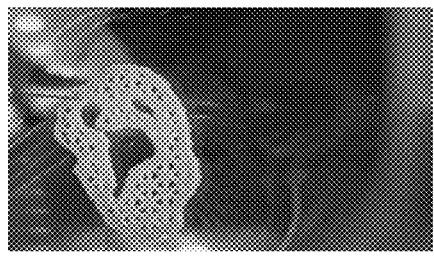
FIG. 8A is a computer modeling diagram of 3D STL file.
Figure 8D:
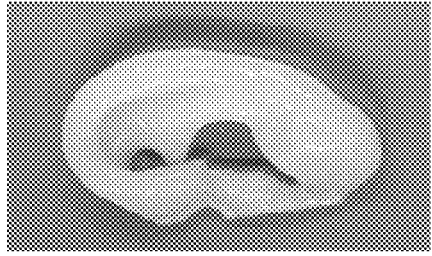
FIG. 8D is a schematic diagram of 10% printing completion of Example 3.
Figure 8B:
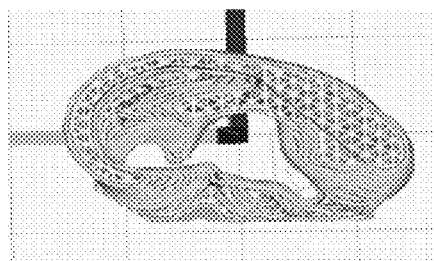
FIG. 8B is an output image in 3D printing format.
Figure 8E:
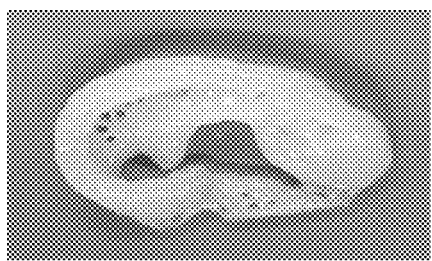
FIG. 8E is a schematic diagram of 60% printing completion of Example 3.
Figure 8C:
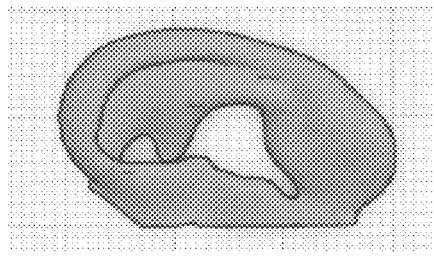
FIG. 8C is a schematic diagram of Example 3 performed the 3D printing.
Figure 8F:
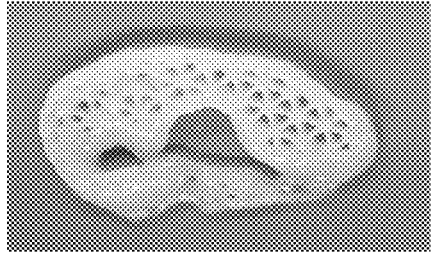
FIG. 8F is a schematic diagram of 100% printing completion of Example 3.

Please refer to FIG. 8A, FIG. 8B, FIG. 8C, FIG. 8D, FIG. 8E and FIG. 8F, wherein FIG. 8A is a computer modeling diagram of 3D STL file. FIG. 8B is an output image in 3D printing format. FIG. 8C is a schematic diagram of Example 3 performed the 3D printing. FIG. 8D is a schematic diagram of 10% printing completion of Example 3. FIG. 8E is a schematic diagram of 60% printing completion of Example 3. FIG. 8F is a schematic diagram of 100% printing completion of Example 3. It can be seen from the result of FIG. 8A to FIG. 8F, the filamentous hydrogel of Example 3 squeezed by the extrusion needle is continuous, and can be stacked in multiple layers to achieve 100% printing completion, indicating that the collagen bio-ink of the present disclosure has the excellent printability and the stackability. Furthermore, the stackability of the collagen bio-ink is proportional to its concentration, if the concentration of the collagen bio-ink is low, the gelation can be added to improve the stackability.

Mechanical Compression Measurement

The collagen bio-ink of Example 5 to Example 7 is filled into the bio-printer, wherein the extrusion needle is the 27 G stainless steel blunt needle, and the solid cylindrical constructs (10 mm in diameter and 10 mm in height) are printed out at 10° C. by the printing speed of 30 mm/s and the extrusion pressure of 33 psi. Next, the printed cylindrical constructs are preserved in the biological incubator at 37° C., and the compression test is performed at different cross-linking time.

Figures 9, 10:
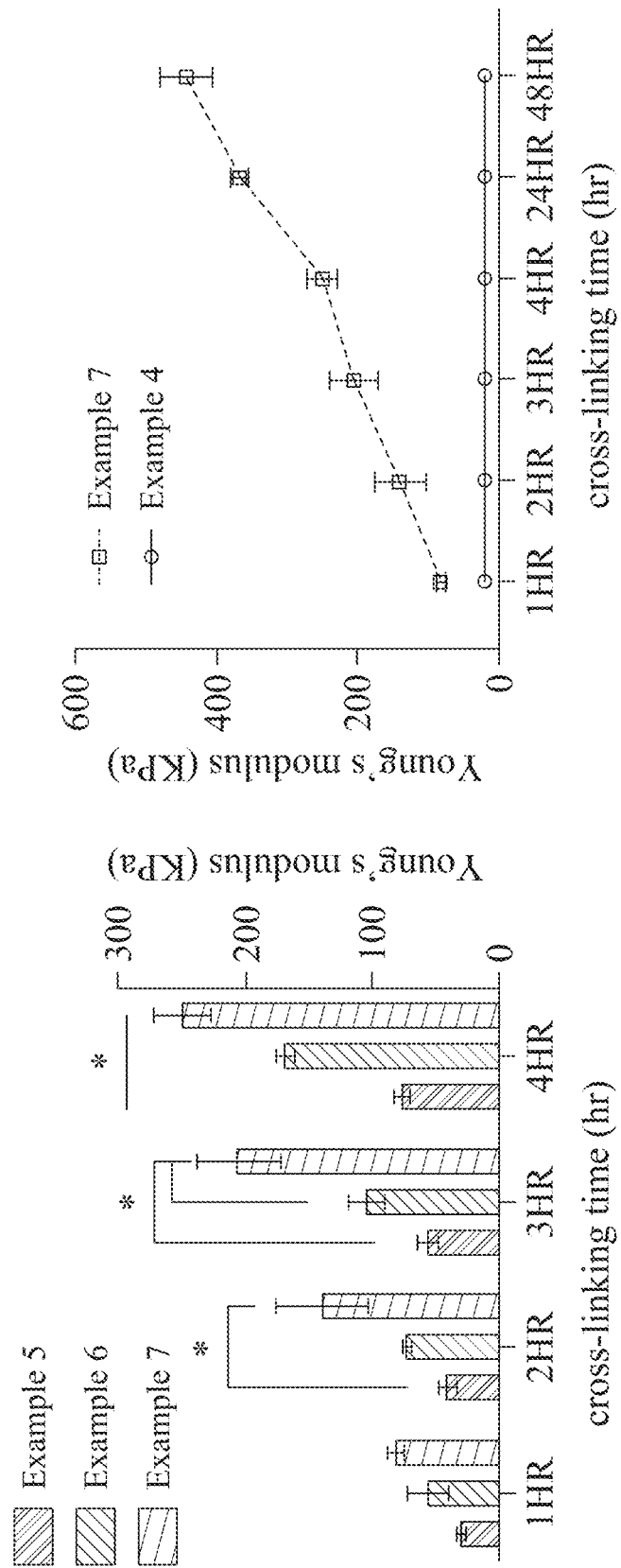
FIG. 9 is a histogram of cross-linking time and Young's modulus of Example 5 to Example 7.
FIG. 10 is a graph of Young's modulus-vs.-cross-linking time of Example 4 and Example 7.

Please refer to FIG. 9 and FIG. 10, wherein FIG. 9 is a histogram of cross-inking time and Young's modulus of Example 5 to Example 7. FIG. 10 is a graph of Young's modulus-vs.-cross-inking time of Example 4 and Example 7. It can be seen from the result of FIG. 9 and FIG. 10, the Young's modulus of Example 7 with the addition of the cross-linking agent is larger than Example 4 without the addition of the cross-linking agent. It can be proved that adding the cross-linking agent can enhance the mechanical strength of the printed product, and the greater the concentration of the cross-linking agent and the longer the cross-linking time, the greater the Young's modulus.

Cell Culture Measurement

The collagen bio-ink of Example 2, Example 3 and Example 8 is placed in the 4° C. refrigerator for 2 hours to 12 hours, respectively. Next, the collagen bio-ink is filed into the bio-printer to operate, wherein the extrusion needle is the 27 G stainless steel blunt needle, and the collagen support is printed out at 10° C. by the printing speed of 30 mm/s and the extrusion pressure of 33 psi. Finally, the printed collagen support is preserved in the biological incubator at 37° C. for 2 hours to heat-solidify the collagen, and then placed on a 24 orifice plate for cell culture (mice C2C12 myoblast, the density of cell is $2 \times 10^5$ μL).

Example 28 to Example 28 is the collagen support printed by Example 3. Example 29 is the collagen support printed by Example 2, and Example 30 is the collagen support printed by Example 8. The aforementioned collagen supports are all disc-shaped, wherein the diameter, the inner diameter height, the wall thickness and the overall wall height of Example 28 to Example 28 is 12 mm, 1.2 mm, 0.8 mm and 3 mm respectively, and the difference of Example 26 to Example 28 is that the width of the groove on the outer layer of the inner diameter of the support (layer height is 0.2 mm), as shown in Table 6. Furthermore, the diameter, the inner diameter height, the wall thickness and the overall wall height of Example 29 and Example 30 is 16 mm, 1.2 mm, 0.8 mm and 5 mm respectively.

TABLE 6

| | width of the groove of the collagen support |
|---|---|
| Example 26 | 0.4 mm |
| Example 27 | 0.8 mm |
| Example 28 | 1.2 mm |

Figure 12:
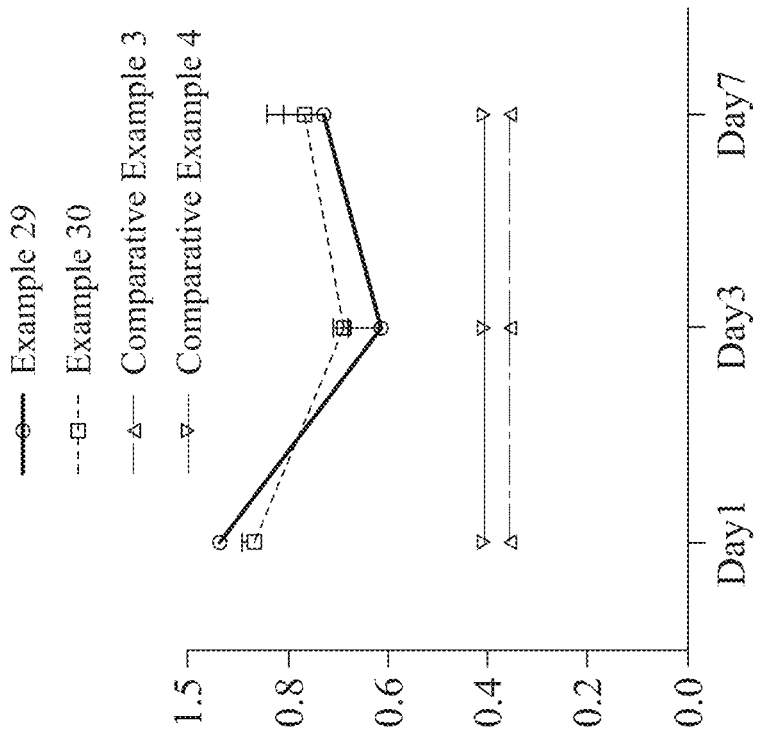
FIG. 12 is a graph of optical density-vs.-different days of Example 29, Example 30, Comparative Example 3 and Comparative Example 4.
Figure 11:
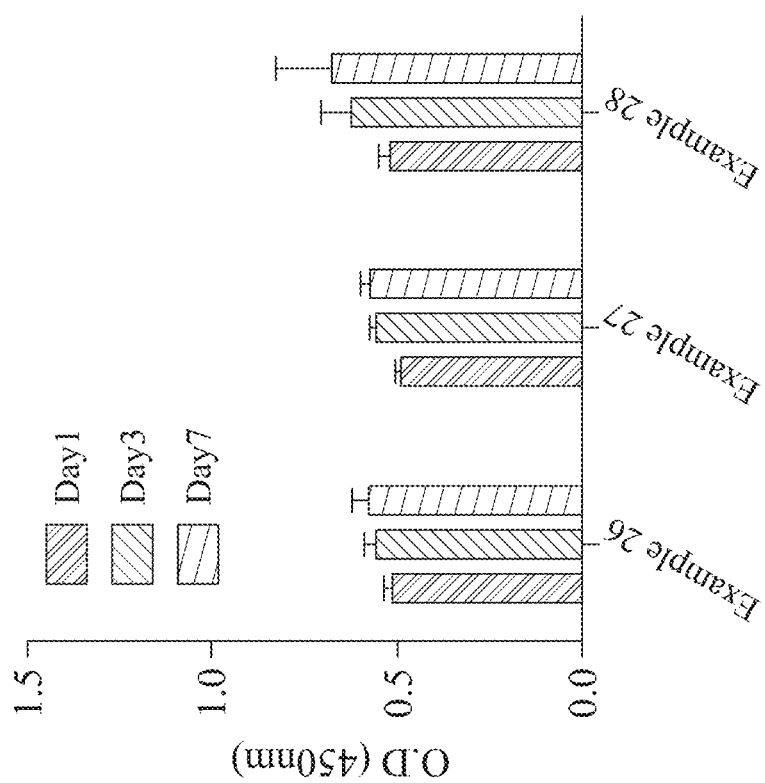
FIG. 11 is a histogram of optical density (O.D.) of Example 26 to Example 28 on different days.

Please refer to FIG. 11 and FIG. 12, wherein FIG. 11 is a histogram of optical density (O.D.) of Example 26 to Example 28 on different days. FIG. 12 is a graph of optical density-vs.-different days of Example 29, Example 30, Comparative Example 3 and Comparative Example 4. Comparative Example 3 is PBS solution, and Comparative Example 4 is DMEM medium solution. It can be seen from the result of FIG. 11, the optical density value of Example 26 to Example 28 does not change much under the same number of days, indicating that different widths of the groove on the outer layer have little effect on the cell survival ratio. Furthermore, it can be seen from the result of FIG. 12, using PBS solution or DMEM medium solution to prepare the collagen bio-ink also has little effect on the cell survival ratio, indicating that the collagen bio-ink of the present disclosure does not cause toxicity to the cells and does not affect the cell survival.

Figure 13B:
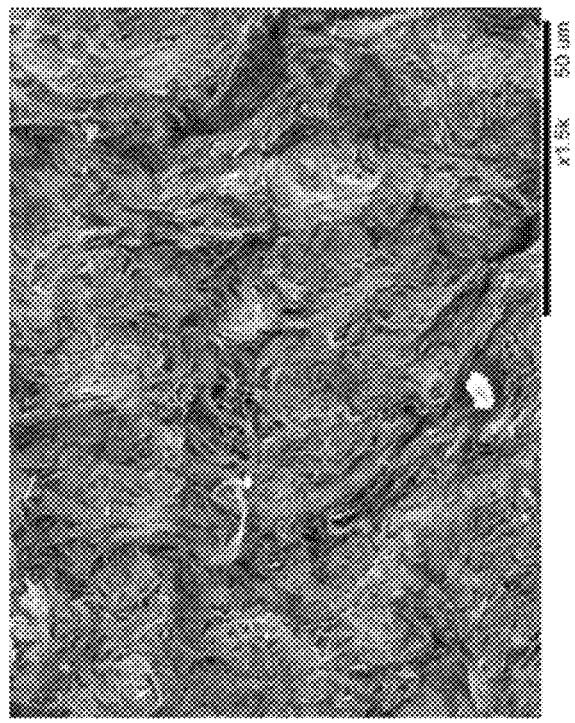
FIG. 13B is a top view image of SEM of Example 29 without cell culture.
Figure 13A:
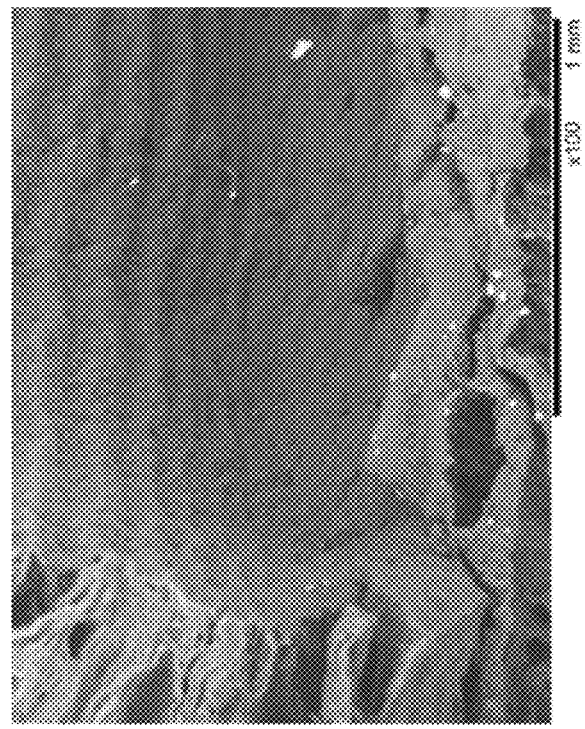
FIG. 13A is a cross-sectional image of SEM of Example 29 without cell culture.
Figure 14B:
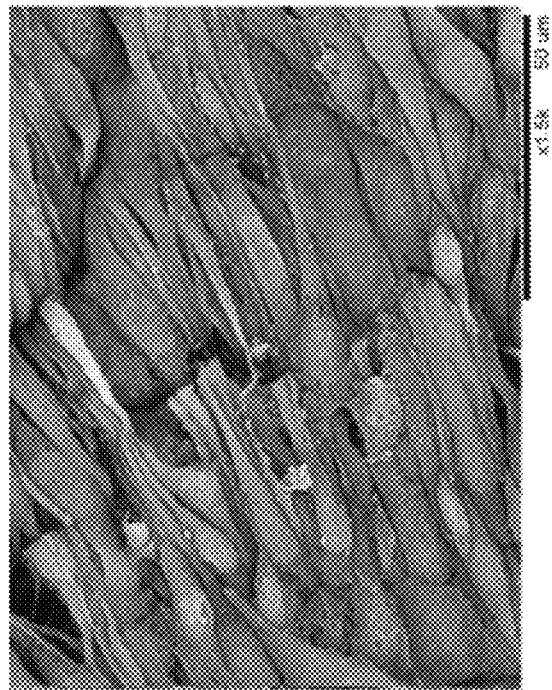
FIG. 14B is a top view image of SEM of Example 29 for seven days cell culture.
Figure 14A:
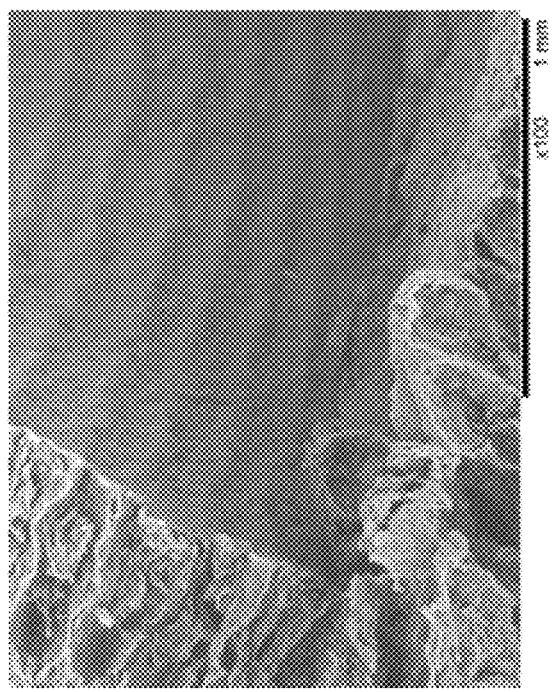
FIG. 14A is a cross-sectional image of SEM of Example 29 for seven days cell culture.

Please refer to FIG. 13A, FIG. 13B, FIG. 14A and FIG. 14B, wherein FIG. 13A is a cross-sectional image of SEM of Example 29 without cell culture. FIG. 13B is a top view image of SEM of Example 29 without cell culture. FIG. 14A is a cross-sectional image of SEM of Example 29 for seven days cell culture. FIG. 14B is a top view image of SEM of Example 29 for seven days cell culture. It can be seen from the result of FIG. 13B, the microstructure of the collagen bio-ink of Example 29 is a fibrous stack. Furthermore, it can be seen from the result of FIG. 14B, after Example 29 performed the cell culture, the layer containing muscle fiber cells is appeared, proving that the collagen bio-ink of the present disclosure has the complete microstructure, and does not cause toxicity to the muscle fiber cell and does not affect the cell survival.

Cell Viability Test

Take 500 μL of the collagen bio-ink of Example 9 to Example 14 to the 24 orifice plate, and place in the incubator for 1 hour. Then, adding 1 mL of DMEM medium solution to perform the cell culture for 24 hours, so as to observe the cell survival ratio by the LIVE/DEAD image.

Figure 15A:
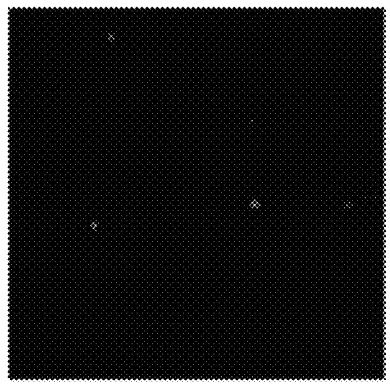
FIG. 15A is a LIVE/DEAD image of Example 9.
Figure 15B:
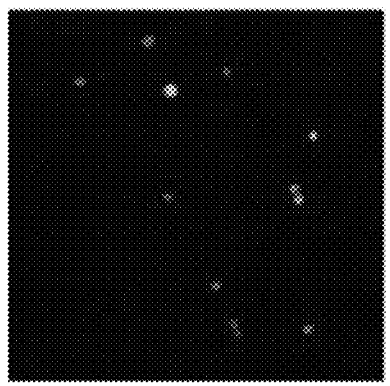
FIG. 15B is a LIVE/DEAD image of Example 10.
Figure 15C:
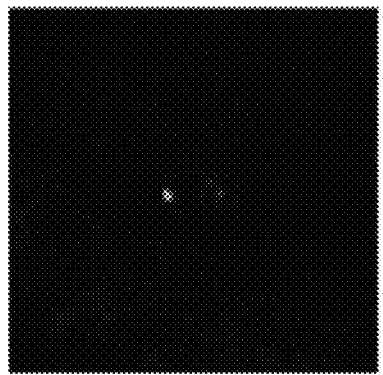
FIG. 15C is a LIVE/DEAD image of Example 11.
Figure 15D:
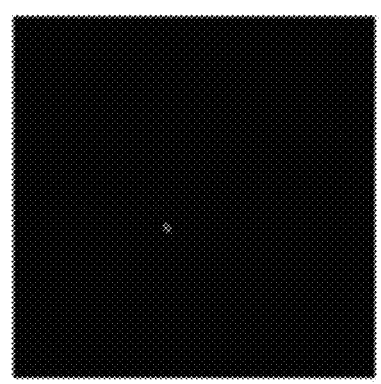
FIG. 15D is a LIVE/DEAD image of Example 12.
Figure 15E:
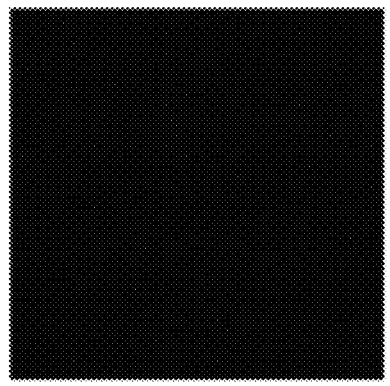
FIG. 15E is a LIVE/DEAD image of Example 13.
Figure 15F:
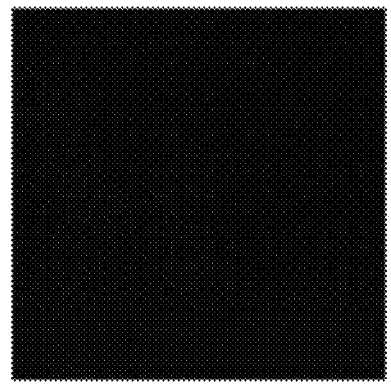
FIG. 15F is a LIVE/DEAD image of Example 14.

Please refer to FIG. 15A, FIG. 15B, FIG. 15C, FIG. 15D, FIG. 15E and FIG. 15F. FIG. 15A is a LIVE/DEAD image of Example 9. FIG. 15B is a LIVE/DEAD image of Example 10. FIG. 15C is a LIVE/DEAD image of Example 11. FIG. 15D is a LIVE/DEAD image of Example 12. FIG. 15E is a LIVE/DEAD image of Example 13. FIG. 15F is a LIVE/DEAD image of Example 14. Moreover, the results obtained from FIG. 15A to FIG. 15F are listed in Table 7. It can be seen from the results of Table 7, the collagen bio-ink of Example 10 with the 2% w/v concentration has the larger cell survival ratio, which is the optimal concentration.

TABLE 7

| | colloidal intensity | cell survival ratio |
|---|---|---|
| Example 9 | low | rare |
| Example 10 | moderate | more |
| Example 11 | moderate | rare |
| Example 12 | vigorous | rare |
| Example 13 | vigorous | none |
| Example 14 | extremely vigorous | none |

Cell Loading Organoid Testing

The collagen bio-ink of Example 22 is filled into the bio-printer to operate, and the bean-like shape of the collagen bio-ink is extruded on the surface of the petri dish, wherein the extrusion needle is the 25 G stainless steel blunt needle. Next, adding 3 mL of DMEM medium solution to cover all the bean-like shape of the collagen bio-ink, and then placing into the incubator, so as to perform the LIVE/DEAD staining on the 1st, 3rd, 5th and 7th days.

Figure 16B:
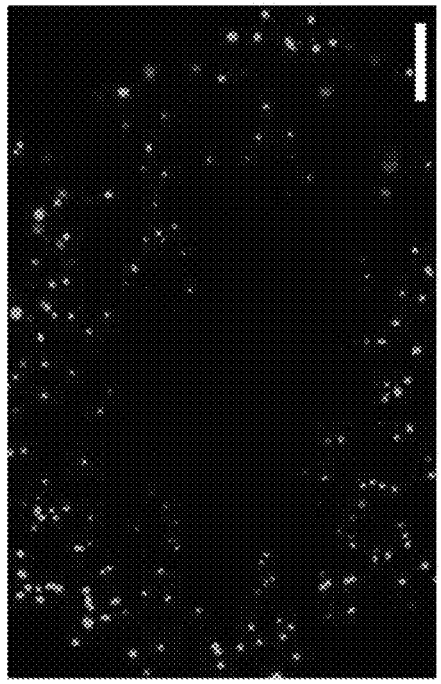
FIG. 16B is a LIVE/DEAD image of Example 22 on the 3rd day.
Figure 16A:
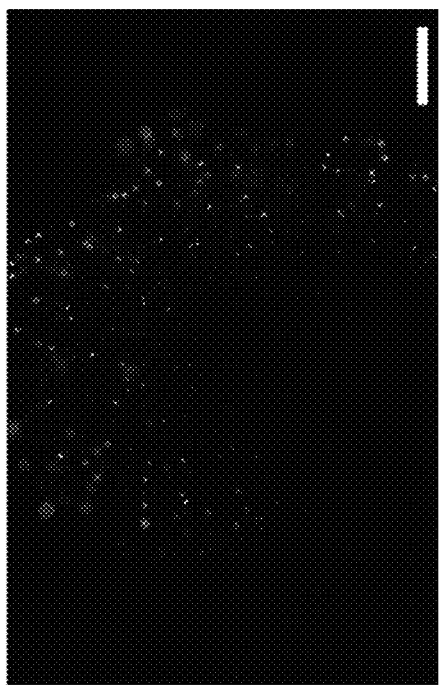
FIG. 16A is a LIVE/DEAD image of Example 22 on the 1st day.
Figure 16D:
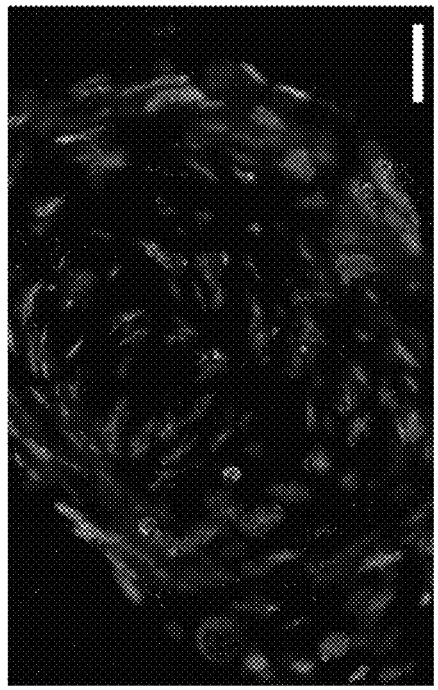
FIG. 16D is a LIVE/DEAD image of Example 22 on the 7th day.
Figure 16C:
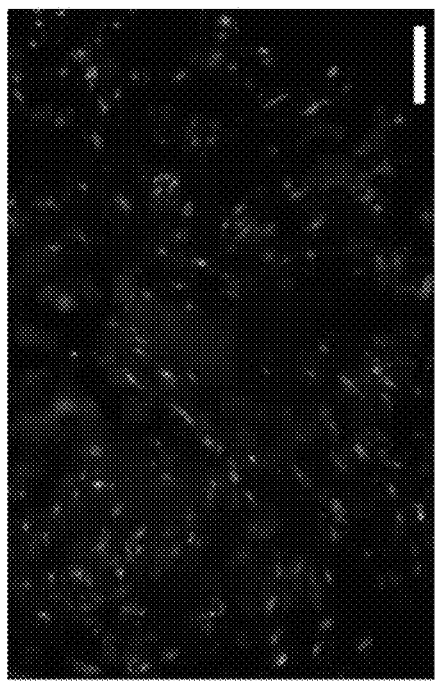
FIG. 16C is a LIVE/DEAD image of Example 22 on the 5th day.

Please refer to FIG. 16A, FIG. 16B, FIG. 16C and FIG. 16D, wherein FIG. 16A is a LIVE/DEAD image of Example 22 on the 1st day. FIG. 16B is a LIVE/DEAD image of Example 22 on the 3rd day. FIG. 16C is a LIVE/DEAD image of Example 22 on the 5th day. FIG. 16D is a LIVE/DEAD image of Example 22 on the 7th day. The bar length in the lower right corner of FIG. 16A to FIG. 16D represents 100 μm.

It can be seen from the result of FIG. 16A to FIG. 16D, the cells in the collagen bio-ink of Example 22 with the 6% w/v concentration survived well, and no obvious dead cells are produced, indicating that in the case of sufficient DMEM medium, the higher concentration of the collagen bio-ink does not affect the cell survival. Furthermore, the L929 cells after the 5th day can be expanded in the collagen bio-ink of Example 22 and maintain the expected phenotype of the cells.

In conclusion, the present disclosure uses the collagen powder to prepare the bio-ink can deploy freely the collagen concentration or mix other functional additives, so that the collagen bio-ink has the excellent preserve condition, the high biocompatibility, the printability and the stackability so as to perform 3D bio-printing. Furthermore, the printed construction has the structural stability and performs the cell culture will not reduce the cell survival rate, so that it is beneficial to prepare the artificial tissues or the supports for the living body using to increase the tissue engineering or the clinical application.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for fabricating a collagen bio-ink, comprising:
   providing a first component, wherein the first component is to fill a collagen powder to a first syringe, and a collagen of the collagen powder is not chemically modified;
   providing a second component, wherein the second component is to fill a neutral solution or an acid solution to a second syringe; and
   performing a mixing step, wherein the first syringe is connected to the second syringe with a Lure lock connector and pushing back and forth to mix the first component and the second component to form a hydrogel and become a collagen bio-ink;
   wherein the collagen bio-ink excludes a maleimide containing polymer;
   wherein a concentration of the collagen bio-ink is 3% w/v to 9% w/v.

2. The method for fabricating the collagen bio-ink of claim 1, wherein the neutral solution is cell culture medium, normal saline or ultrapure water.

3. The method for fabricating the collagen bio-ink of claim 1, further comprising:
   performing a neutralization step, wherein after the acid solution mixed with the collagen powder, a buffer salt solution, an alkaline substance or a conjugated acidic base pair is added to neutralize acidic level.

4. The method for fabricating the collagen bio-ink of claim 1, wherein the first component further comprises a gelatin powder.

5. The method for fabricating the collagen bio-ink of claim 4, wherein a ratio of the collagen powder to the gelatin powder is 10:1.

6. The method for fabricating the collagen bio-ink of claim 1, further comprising:
   performing an adding step, wherein a functional solution or a cell solution is added to the collagen bio-ink.

7. The method for fabricating the collagen bio-ink of claim 6, wherein the functional solution is a medicine, a growth factor or a cross-linking agent solution.

* * * * *